United States Patent [19]

Partridge, Jr. et al.

[11] 4,038,272
[45] July 26, 1977

[54] STEREOSPECIFIC SYNTHESES OF 24R,25- AND 24S,25-DIHYDROXYCHOLESTEROL AND ALKANOYL DERIVATIVES THEREOF

[75] Inventors: John Joseph Partridge, Jr.; Milan Radoje Uskokovic, both of Upper Montclair, N.J.

[73] Assignee: Hoffmann-La Roche Inc., Nutley, N.J.

[21] Appl. No.: 623,859

[22] Filed: Oct. 20, 1975

[51] Int. Cl.² .......................... C07J 71/00; C07J 53/00
[52] U.S. Cl. .......................... 260/239.55 R; 260/397.2
[58] Field of Search ........................................ 260/397.2

[56] References Cited

U.S. PATENT DOCUMENTS

| 3,822,254 | 7/1974 | Partridge et al. | 260/397.2 |
| 3,928,397 | 12/1975 | Ilekawa et al. | 260/397.2 |
| 3,959,320 | 5/1976 | Salmond | 260/397.2 |

OTHER PUBLICATIONS

"Steroid Reactions" by Djerassi et al. (1963), p. 160.

*Primary Examiner*—Elbert L. Roberts
*Attorney, Agent, or Firm*—Samuel L. Welt; George M. Gould; Raymond R. Wittekind

[57] ABSTRACT

Stereospecific syntheses of 24R,25- and 24S,25-dihydroxycholesterol and alkanoyl derivatives thereof, intermediates in the preparation of biologically important metabolites of Vitamin $D_3$, are described.

63 Claims, No Drawings

STEREOSPECIFIC SYNTHESES OF 24R,25- AND 24S,25-DIHYDROXYCHOLESTEROL AND ALKANOYL DERIVATIVES THEREOF

BACKGROUND OF THE INVENTION

The isolation and characterization of 24,25-dihydroxycholecalciferol, 24,25-dihydroxyvitamin $D_3$ (M. F. Holick, et al., Biochemistry, II 4251 (1972), and the subsequent finding that this second most abundant metabolite of vitamin $D_3$ (J. L. Omdahl and H. F. DeLuca, Physiological Reviews, 53, 327 (1973) preferentially stimulates intestinal calcium transport without, at comparable dose levels, mobilizing bone calcium and is biologically synthesized in the kidney at the expense of the production of 1 $\alpha$, 25-dihydroxycholecalciferol, the potent, rapid-acting, natural metabolite of vitamin $D_3$ (J. L. Omdahl and H. F. DeLuca, supra), prompted fairly extensive investigation of the physiological role played by this metabolite (see for example, H. K. Schomes and H. F. DeLuca, Vitamins and Hormones, 32, 385 (1974). These investigation have been hampered by the minute amounts available from natural sources and the lack of information concerning the stereochemistry of the metabolic hydroxyl group at C-24 and the effect of the configuration of this group on the biological activity exhibited by 24,25-dihydroxycholecalciferol.

Recently, M. Seki, et al. (Chem. Pharm. Bull. (Japan), 21, 2783 (1973) described the non-stereoselective conversion of desmosterol acetate to 24,25-dihydroxycholesterol by either epoxidation with m-chloroperbenzoic acid followed by hydrolysis or hydroxylation with osmium tetroxide followed by reductive hydrolysis. The diol of undefined stereochemical composition at C-24, as well as the epoxide were subsequently used for the preparation of 24R,25- and 24S,25-dihydroxycholecalciferol in a process which involves separation of the epimeric 24,25-epoxides or 24,25-diols followed by the established steps for the conversion of chlolesterol derivatives to vitamin $D_3$ metabolites. Shortly thereafter, H. -Y. Lam, et al. (Biochemistry, 12, 4851 (1973)) reported a non-steroselective synthesis of 24,25-dihydroxycholecalicferol starting from 3$\beta$-acetoxy-27-nor-5-cholesten-25-one and proceeding via 24,25-dihydroxycholesterol. J. Redel, et al. (Compt. Rend, Acad. Soc. (Paris), 2781, 529 (1974)) also disclosed a non-stereoselective process for the preparation of the vitamin $D_3$ metabolite. The latter process started with desmosterol acetate, proceeded through an undetermined mixture of 24R,25- and 24S,25-dihydroxycholesterols and gave an extremely poor (about 1%) yield of a undefined mixture of 24F,25- and 24S,25-dihydroxycholecalciferol. Thus sterespecific syntheses of 24R, 25- and 24S,25-dihydroxycholecalciferol utilizing 24,25-dihydroxycholesterol derivatives of known stereochemistry at C-24 -overcoming the deficiencies of the prior art processes and making this important metabolite of vitamin $D_3$ readily available for biological, clinical and therapeutic use would represent a major contribution to the advancement of the state of the art in the vitamin D field.

DETAILED DESCRIPTION OF THE INVENTION

The present invention relates to novel, efficient, stereospecific methods for the preparation of 24R, 25- and 24S,25-dihydroxycholesterols and alkanoyl derivatives thereof starting from the 6$\beta$-hydroxy or substituted -6$\beta$-hydroxy-25-(2-tetrahydropyranyloxy)-3$\alpha$,5-cyclo-5$\alpha$-cholest-23-yne, readily preparable from the naturally occurring (readily available and relatively inexpensive) stigmosterol. More particularly, the present invention relates to methods of synthesizing 24R,25 and 24S,25-dihydroxycholesterols, comprising the key steps of stereospecifically reducing 25-hydroxy-6$\beta$-hydroxy or substituted-6$\beta$-hydroxy-3$\alpha$, 5-cyclo-5$\alpha$-cholest 23-yne to 25-hydroxy-6$\beta$-hydroxy or substitued-6$\beta$-hydroxy3$\alpha$-5-cyclo-5$\alpha$-cholest-23(E)-ene, stereospecifically epoxidizing 25-hydroxy-76$\beta$-hydroxy ro substituted-6$\beta$-hydroxy-3$\alpha$,5-cyclo-5$\alpha$-cholest-23 (E)-ene to 23R,24S-epoxy-25-hydroxy- 6$\beta$-hydroxy or substitued hydroxy-3$\alpha$,5-cyclo-5$\alpha$-cholestane and regiospecifically cleaving 23R, 24S-epoxy-25-hydroxy-6$\beta$-hydroxy or substituted-6$\beta$-hydroxy-3$\alpha$,5-cyclo-5$\alpha$-cholestant to 24S,25-dihydroxy-6$\beta$-hydroxy or substitute-6$\beta$-hydroxy-3 $\alpha$,5-cyclo-5$\alpha$-cholestane and stereospecifically reducing 25-hydroxy- b6$\beta$-hydroxy or substituted-6$\beta$-hydroxy-3$\alpha$,5-cyclo-5$\alpha$-cholest-23-yne to 25-hydroxy-6$\beta$-hydroxy or substituted-6$\beta$-hydroxy-3$\alpha$,5-cyclo-5$\alpha$-cholest-23(Z)-ene, stereospecifically epoxidizing 25-hydroxy-6$\beta$-hydroxy or substituted-6$\beta$-hydroxy-3$\alpha$,5-cyclo-$\alpha$-cholest-23-(E)-ene to 23R,24R-epoxy-25-hydroxy-6$\beta$-hydroxy or substituted-6$\beta$-hydroxy-3$\alpha$,5-cyclo-5$\alpha$-cholestane and regiospecifically cleaving 23R,24R-epoxy-25-hydroxy-6$\beta$-hydroxy or substituted-6$\beta$-hydroxy-3$\alpha$, 5-cyclo-5$\alpha$-cholestane to 24R,25-dihydroxy-662or substituted-6$\beta$-hydroxy-3 $\alpha$,5-cyclo-5$\alpha$-cholestane.

The present invention also relates, more paticularly, to methods of synthesizing 24R,25 and 24S,25dihydroxycholesterol comprising the key steps of regiospecifically and stereospecifically hydroxylating 25-hydroxy-6$\beta$-hydroxy or substituted-6$\beta$-hydroxy-3$\alpha$,5-cyclo-5$\alpha$-cholest-23(E)-ene to 24S,25-dihydroxy-6 $\beta$-hydroxy or substituted -6$\beta$-hydroxy-3$\alpha$,5-cyclo-5$\alpha$-cholestant and regiospecifically and stereospecifically hydroxylating 25-hydroxy-6$\beta$-hydroxy or substituted-6$\beta$-hydroxy-3$\alpha$,5-cyclo-5$\alpha$-cholest-23(Z)-ene to 24R,25 -dihydroxy-6$\beta$-hydroxy or substituted hydroxy-3$\alpha$,5-cyclo-5$\alpha$-cholestane, respectively.

As used throughout the specification and the appended claims, the term "alkyl group" refers to a monovalent substituent consisting solely of carbon and hydrogen of from 1 to 20 carbon atoms which may be straight or branched chain. Examples of alkyl groups are methyl, ethyl, n-propyl, i-propyl, tert-butyl, hexyl, octyl and so forth. The term "alkylene group" refers to a divalent substituent consisting solely of carbon and hydrogen of from 1 to 20 carbon atoms which may be straight or branched chain and whose free valences are attached to two distinct groups. Examples of alkylene groups are methylene, ethylene, propylene and so forth. The term"alkoxy group" refers to a monovalent substituent which consists of an alkyl group linked through an ether oxygen having its free valence bodn from the ether oxygen. Examples of alkoxy groups are methoxy, ethoxy, isopropoxy, tert-butoxy and so forth. The term "phenyl alkoxy" refers to an alkoxy group which is substituted by a phenyl ring. Examples of phenyl alkoxy groups are benzyloxy, 2-phenylethoxy,4-phenylbutoxy, and so forth, The term "alkanoyloxy group" refers to the residue of an alkylcarboxylic acid formed by removal of the hydrogen from the hydroxyl portion of the carboxyl group. Examples of alkanoyloxy groups are formyloxy, acetoxy, butyryloxy, hexanoyloxy, and so forth. The term "substituted", as applied to phenyl refers to phenyl which is substituted with one or more of the following groups: alkyl, halogen (i.e., fluorine, chlorine, bromine or iodine), nitro, cyano, trifluoromethyl, and so forth. The term "lower" as applied to any of the aforementioned groups, refers to those groups having from 1 to 8 carbon atoms.

In the formulae presented herein, the various substituents are illustrated as joined to the steriod nucleus by one of three notations: a solid line (—) indicating a substitutent which is in the beta-orientation (i.e., above the plane of the molecule), a dotted line (---) indicating a substitutent which is in the alpha-orientation (below the plane of the molecule), or a wavy line ( ) indicating a substituent which may be in the alpha or beta-orientation. The formulae have all been drawn to show the compounds in their absolute stereochemical configuration. Since the starting material, 6β-hydroxy or substituted-6β-hydroxy-25-(2-tetrahydropyranyloxy)-3α,5-cyclo-5α-cholest-23-yne, is derived from naturally occurring, stigmasterol, the products exist in the single absolute configuration depicted herein. However, the processes of the present invention are intended to apply as well to the synthesis of steriods of the unnatural and racemic series, i.e., the enantiomers of the compounds depicted herein and mixtures of both. Thus, one may being the synthesis utilizing unnatural or racemic starting materials to prepare unnatural or racemic products, respectively. Optically active products can then be prepared by resolution of the racemic products utilized in the preparation thereof by standard resolution techniques well-known in the steroid art.

The nomenclature adopted to defined the stereochemistry about the 23,24-double bond and the absolute configuration of substituents bound to carbon atoms 23 and 24 of the steroid nucleus is described in The Journal or Organic Chemistry, 35, 2849 (1970) under the title "IUPAC Tentative Rules for the Nomenclature of Organic Chemistry. Section E. Fundamental Stereochemistry". For example, the sequence rule-preferred groups attached to carbon atoms 23 and 24 in compound III are on opposite sides of the reference plane and therefore the stereochemistry about the 23,24-double bond is denoted by the prefix E, and since the handedness of the sequence rule-preferred groups bound to carbon atom 24 in compound V is countercockwise, the absolute stereochemistry is denoted by the prefix S.

The Greek letter ξ (xi) when used in conjunction with the name of a vitamin D intermediate or metabolite denotes that the substituent to which it refers is of undefined stereochemistry.

The starting material, a compound of the formula

I

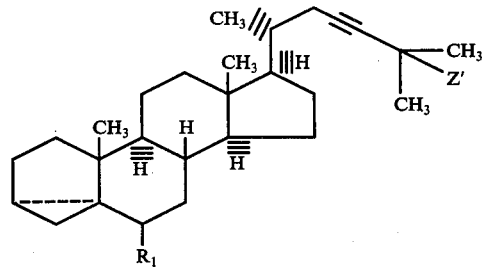

wherein $R_1$ is hydroxy, lower alkoxy, phenyl lower alkoxy, lower alkanoyloxy or benzoyloxy and Z' is a group of the formula

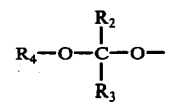

wherein $R_2$ is hydrogen or lower alkyl, $R_3$ and $R_4$ each taken independently are lower alkyl and $R_3$ and $R_4$ taken together are lower alkylene of from 3 to 6 carbon atoms, for the preparation of 24R,25- and 24S,25-dihydroxy-cholesterol is prepared by the method described in U.S. Pat. No. 3,822,254, issued July 2, 1974.

In the first step of the synthetic sequence, the C-25 tetrahydropyranyloxy group of a compound of formula I is selectively cleaved to afford a compound of the formula

II

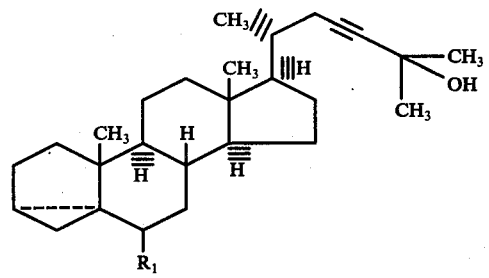

wherein $R_1$ is as above,
in which the 3-hydroxy or 3-alkanoyloxy-Δ⁵ system of the final cholesterol derivatives is protected as the i-steroid function and in which the 23,24-yne group provides the means for the stereospecific introduction of the C-24 hydroxyl group.

This transformation is conveniently performed by treating a compound of formula I with a catalytic amount of a strong acid in an appropriate solvent. For example, to prepare 25-hydroxy-6β-methoxy-3 α,5-cyclo-5α-cholest-23-yne, the compound of formula II wherein $R_1$ is methoxy, one would employ methanol as the appropriate solvent and sulfuric or sulfonic acids, such as benzenesulfonic acid, p-toluenesulfonic acid and the like as the catalytic strong acid.

In the second and one of the two crucial stereospecific steps of the process for the preparation of 24S,25-dihydroxy-6β-methoxy-3α,5-cyclo-5α-cholestane, a compound of formula II, is reduced with a complex metal hydride in a suitable inert organic solvent at an elevated temperature to a compound of formula III

III

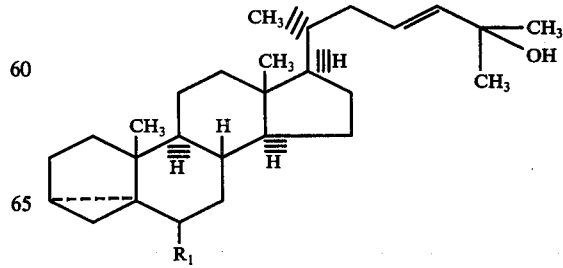

wherein R₁ is as above,
and in which the protons attached to carbon atoms 23 and 24 bear a trans-relationship to each other, i.e., the compound in which the configuration about the 23,24-double bond is denoted by the prefix E.

Suitable complex metal hydrides for the purposes of converting compounds of formula II to compounds of formula III include alkali metal aluminum hydride reducing agents such as lithium aluminum hydride; mono- and di-(lower alkoxy) alkali metal aluminum hydrides such as, for example, lithium mono-(tert-butoxy)aluminum hydride and lithium bis-(tert-butoxy)aluminum hydride, sodium bis-(2-methoxyethoxy)aluminum hydride; and so forth. Suitable inert organic solvents for the reduction include ethereal solvents such as diethyl ether, dimethoxyethane, dimethoxyethoxyethane, tetrahydrofuran and dioxane. The reduction is conveniently carried out at a temperature between about 50°–70° C.

While the quantity of the complex metal hydride is not narrowly critical and can vary between about 1/2 and 10 moles relative to the compound being reduced, it is generally preferred to utilize between about 1 and 5 moles of the complex metal hydride relative to the substrate. A molar ratio of complex metal hydride to substrate of about 2 is most preferred.

The stereospecific reduction of the 23,24-triple bond of a compound of formula II is preferably performed using an alkali metal aluminum hydride in a cyclic ethereal solvent at a reaction temperature of about 50° C to 70° C. It is most preferable to use lithium aluminum hydride in tetrahydrofuran at about 70° C.

During the reduction of the acetylenic linkage of a compound of formula II to a double bond of a compound of formula III, an alkanoyloxy or benzoyloxy group (R₁) in the 6-position of the i-steroid molecule may be partially reduced to the corresponding 6-hydroxy group. The carbinol may be carried through the reaction sequence as such, or the hydroxy group may be reacylated by methods well-known in the art at some convenient stage in the process.

To prepare the corresponding cis-isomer of 25-hydroxy-6β-hydroxy or substituted -6β-hydroxy-3α,5-cyclo-5α-cholest-23(Z)-ene, i.e., a compound of formula IV

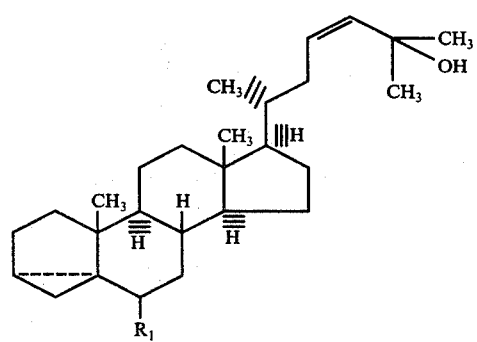

IV wherein R₁ is as above,
and in which the configuration of the 23,24-double bond is denoted by the prefix Z, a compound of formula II is hydrogenated in the presence of a suitable hydrogenation catalyst and a suitable solvent. Among catalysts suitable for the stereospecific hydrogenation are nickel and noble metal catalysts such as, for example platinum, palladium, rhodium and the like, free or supported on a suitable carrier such as, for example, carbon, calcium carbonate, strontium carbonate, alumina and the like. Also included among catalysts suitable for the stereospecific hydrogenation are partially deactivated catalysts composed of noble metals, free or supported, and poisoned with a heavy metal and an aromatic nitrogen heterocycle such as, for example, a Lindlar catalyst composed of palladium-on-calcium carbonate poisoned with lead diacetate and quinoline and the like. Generally, a palladium catalyst is preferred.

The quantity of catalyst which may be used is not narrowly critical and the amount of catalyst including the support may vary from about 0.01 to about 2.0 weight percent relative to the compound being reduced. Generally, it is preferred to use between about 0.05 and 0.5 weight percent of catalyst.

As solvents suitable for the hydrogenation reaction, there may be mentioned, among others, ethers such as diethyl ether, tetrahydrofuran, dioxane, dimethoxyethane, dimethoxyethoxyethane and the like, alcohols such as ethanol, methanol, 2-propanol and the like; esters such as methyl acetate, ethyl acetate and the like; organic carboxylic acids such as acetic acid and the like; and so forth. It is preferred to use methanol as the hydrogenation solvent.

While the conditions of temperature and pressure for the partial catalytic hydrogenation of the acetylenic linkage are not narrowly critical, it is preferred to carry out the hydrogenation reaction at a pressure falling within the range from about 1 atmosphere to about 5 atmospheres of hydrogen and at a temperature from about 0° C to about 100° C, depending upon solvent medium and the pressure employed. Generally, it is preferred to perform the hydrogenation reaction at a pressure of about 1 to about 3 atmospheres of hydrogen and at a temperature between about 0° C to about 50° C.

The partial stereospecific hydrogenation of the acetylenic linkage of compounds of formula II to olefins of formula IV having the Z-configuration is most preferably carried out in the presence of the Lindlar catalyst described by H. Lindlar and R. Dubuis in "Organic Syntheses", Coll., Vol. V, John Wiley and Sons, New York, N.Y., 1973, pages 880–883.

To prepare 24S,25-dihydroxy-6β-hydroxy or substituted-6β-hydroxy-3α,5-cyclo-5α-cholestane, a compound of formula V

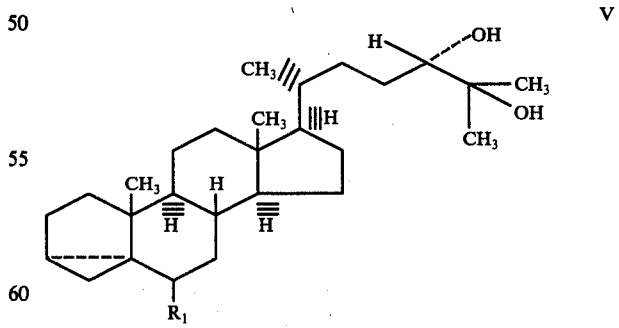

V wherein R₁ is as above,
and the absolute stereochemistry at C-24 is S, a compound of formula III in which the configuration of the 23,24-double bond is trans, may be either directly stereospecifically hydroxylated or first stereospecifically epoxidized to a compound of formula VI

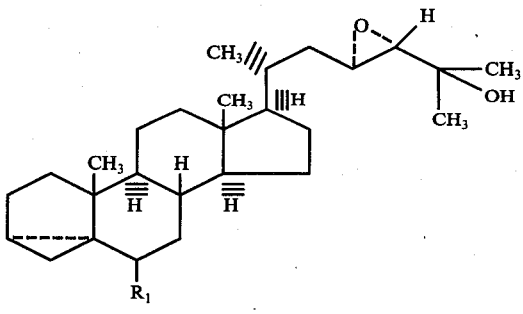

wherein $R_1$ is as above,
and the absolute stereochemistry at C-23 and C-24 is R and S, respectively, followed by sterospecific reduction cleavage of the epoxy system.

In the former, compound of formula III is first hydroborated with a borane of formula VII

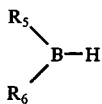

wherein $R_5$ and $R_6$ each taken independently are hydrogen, alkyl or cycloalkyl and $R_5$ and $R_6$ taken together are lower alkylene
to afford an i-steroidyl borane of formula VIII

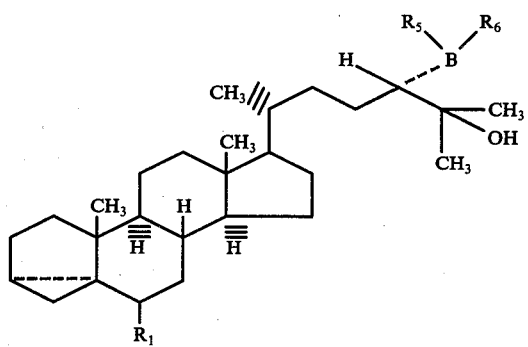

wherein $R_1$, $R_5$ and $R_6$ are as above,
which without isolation, is oxidized to the i-steroidyl diol of formula V.

The hydroboration reaction may be conveniently performed by contacting a compound of formula III dissolved in a suitable inert organic solvent with a borane of formula VII also dissolved in a sutiable organic solvent at a reduced temperature and thereafter allowing the reaction temperature to increase to about ambient temperature. Suitable inert organic solvents for this transformation include aromatic solvents such as benzene, toluene and the like, ethereal solvents such as diethylether, dimethoxyethane, dimethoxyethoxyethane, tetrahydrofuran, dioxane and the like. Ethereal solvents are preferred. Among the boranes which are useful for the hydroboration reaction may be mentioned borane, bis-(3-methyl-2-butyl)borane (disiamylborane), 2,3-dimethyl-2-butylborane (thexylborone), dicyclohexylborane, 9-borobicyclo-[3.3.1]nonone and the like. Borane, disiamylborane and thexylborane are preferred.

The temperature at which the hydroboration reaction is performed is not narrowly critical. It is conveniently carried out by mixing the substrate and reagent at below or about 0° C and then allowing the reaction mixture to warm to about room temperature.

While the molar proportion of the borane to i-steroidyl olefin of formula III is not cirtical and molar ratios of about 1 to about 10 may be utilized, it is preferoble to use about 3 to about 8 moles of the hydroborating agent for each mole of olefin, especially with the more volatile boranes.

Generally, it is most preferred to perform the hydroboration reaction in tetrahydrofuran at an initial reaction temperature of about 0° C and a final reaction temperataure of 25° C using about 4 moles of the borane for each mole of i-steroidyl olefin of formula III.

While the intermediate i-cholesteryl borane of formula V may be isolated from the hydroboration reaction mixture prior to oxidation, the borane is generally oxidized to the carbinol without isolation, after destruction of excess borane by the addition of ice-water. The oxidation is conveniently carried out either by introducing the theoretical amount of oxygen (based on the number of moles of i-cholesteryl borane) at about 0° C or excess aqueous alkaline hydrogen peroxide at a reaction temperature of about ° C 50° C. Aqueous alkaline hydrogen peroxide is preferred.

As alkali for the oxidation reaction, there may be mentioned, among others, alkali metal hydroxides such as sodium hydroxide, potassium hydroxide and the like, and alkaline earth hydroxides such as as calcium hydroxide, barium hydroxide and the like. Alkali metal hydroxides are preferred. Sodium hydroxide is most preferred. The amount (relative to i-cholesteryl borane) of aqueous alkali which may be empolyed is not cirritical and can vary between about 1 to about 10 moles of aqueous alkali for each mole of borane. A relative amount of aqueous alkali of about 2 to about 8 is preferred; a relative amount of aqueous alkali of about 4 is most preferred. The concentration of aqueous alkali is also not critical and can vary between about 0.1 to about 10 molar. A concentration of aqueous alkali of about 1 to about 7 molar is preferred. A concentration of aqueous alkali of about 3 molar is most preferred.

Synthetic applications of hydroboration and oxidationof boranes have been extensively reviewed by H. C. Brown in "Hydroboration", W. A. Benjamin, Inc., New York, N.Y., 1962, and "Boranes in Organic Chemistry", Cornell University Press, Ithaca, N.Y., 1972.

In the latter, an i-cholesteryl derivative of formula III having a 23, 24-double bond is stereospecifically epoxidized with a lower alkyl or aryl lower alkyl hydroperoxide in the presence of a catalytic amount of vanadyl acetylacetonate of formula IX

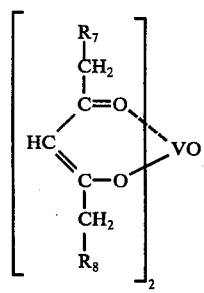

wherein $R_7$ and $R_8$ are hydrogen or lower alkyl, in a suitable inert organic solvent at a reduced temperature.

Suitable lower alkyl hydroperoxides include methyl-,ethyl-,propyl-, 2-propyl-,sec-butyl-and tert-butylhydroperoxides and the like. Suitable aryl lower alkyl hydroperoxides include cumyl hydroperoxide. Branched chain hydroperoxides are preferred. tert-Butyl-hydroperoxide is most preferred. Suitable inert organic solvents include aromatic solvents such as benzene, toluene and the like, and halogenated hydrocarbons such as methylene chloride, chloroform, carbon tetrachloride and the like. Aromatic hydrocarbons are preferred. Toluene is most preferred.

Among vanadyl acetylacetonates of formula IX suitable for the stereospecific epoxidation reaction, there may be mentioned those wherein $R_7$ and $R_8$ are each independently and simultaneously hydrogen and lower alkyl having one to 6 carbon atoms. Vanadyl acetylacetonates of formula IX wherein $R_7$ and $R_8$ are simultaneously hydrogen or lower alkyl are preferred. Vanadyl acetylacetonate is most preferred.

The amounts of lower alyl hydroperoxide and vanadyl acetylacetonate of fromula IX both relative to amount of i-cholesteryl olefin of formula III which may be utilized in the epoxidation reaction are not narrowly critical and can vary from 1 to about 5 moles of lower alkyl hydroperoxide to about 0.01 to about 10 weight percent of the catalyst. The expoxidation reaction is preferably carried out using about 2.5 molar excess of the hydroperoxide and about 1 weight percent of the vanadyl catalyst.

Vanadyl acetylacetonates of formula IX can be prepared by the method described by R. A. Rowe, et al., Inorganic Synthesis, 5, 113 (1957) and references cited therein.

The sterospecific epoxidation of 23, 24-double bond of a compound of formula III is conveniently performed by mixing the reagents and substrate at an initial reaction temperature between about $-100°$ C and about $-50°$ C and then allowing the reaction temperature to slowly raise to between $-40°$ C and $+20°$ C. An initial reaction temperature of about $-80°$ C and a final reaction temperature of about $-20°$ is most preferred.

In the next step of the reaction sequence, the epoxide of formula VI is regiospecifically cleaved to the i-cholesteryl diol of formula V. This transformation is accomplished by reduction of the epoxide with a complex metal hydride reducing agent suspended in a suitable inert organic solvent.

Suitable complex metal hydride reducing agents for this purpose include alkali metal aluminum hydrides such as lithium aluminum hydride; mono-, di- or tri-(lower alkoxy) alkali metal aluminum hydrides such as for example, lithium tris(tert butoxy) aluminum hydride; mono-, di- or tri(lower alkoxy lower alkoxy) alkali metal aluminum hydrides such as, for example, sodium bi (2-methoxyethoxy) aluminum hydried; di(-lower alkyl) aluminum hydrides such as, for example, diisobutyl aluminum hydride; and so forth. A particularly preferred complex metal reducing agent for this purpose is lithium aluminum hydried. Suitable solvents for the reductive cleavage reaction include ethereal solvents such as diethylether, dimethoxyethane, dimethoxyethoxyethane, tetrahydrofuran and dioxane. Tetrahydrofuran is most preferred. The reductive cleavage reaction is conveniently carriedout at a temperature between about $-20°$ C to about $50°$ C, most preferably between about $0°$ C and about $25°$ C.

24R,25-Dihydroxy-6β-hydroxy or substituted-6β-hydroxy-3α,5-cyclo-5α-cholestanes, compounds of formula X

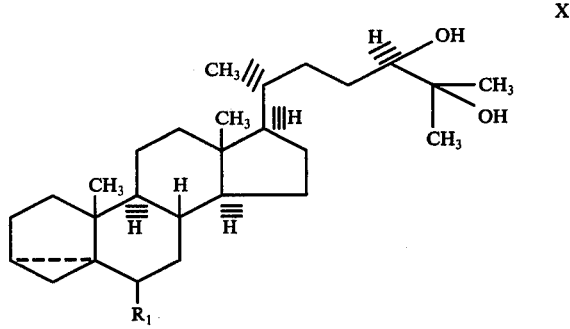

wherein $R_1$ is as above,
and the absolute configuration at C-24 is R, are prepared by the aforementioned processes for the preparation of a compound of formula V, in which the absolute configuration at C-24 is S, utilizing a compound of formula IV, in which the configuration of the 23,24-double bond is cis, instead of a compound of formula III, in which the configuration of the 23,24-is trans. In the process for the preparation of a compound of formula X, a compound of formula IV is either directly hydroxylated to the i-cholesteryl diol of formula X or first converted to the i-cholesteryl epoxide of formula XI

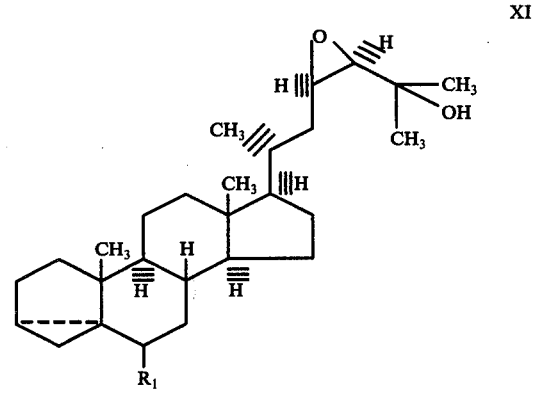

wherein $R_1$ is as above,
and the absolute configuration of the epoxy group is 23R,24R, and then reductively cleaved to a compound of formula X.

As in the case of the conversion of the trans-olefin of formula III to the S-alcohol of formula V, the direct hydroxylation is effected by the hydroboration-oxidation method and the indirect hydroxylation by the epoxidation-reduction cleavage process.

The final step of the stereospecific synthesis of 24R,25- and 24S,25-dihydroxycholesterol and the alkanoyl derivatives thereof involves the retro-i-rearrangement of compounds of formulas V and X to cholesterols of formula XII

XII

-continued

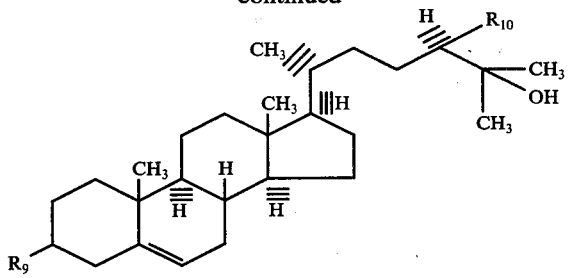

wherein $R_9$ and $R_{10}$ are hydroxy or lower alkanoyloxy,
and the absolute configuraton at C-24 is R, and XIII

XIII

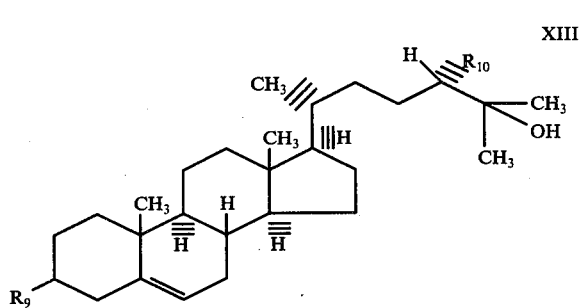

wherein $R_9$ and $R_{10}$ are as above,
and the absolute configuration at C-24 is S, respectively. These conversions can be accomplished by treating the i-cholesteryl diols with an acid in a suitable solvolytic medium. For example, to prepare 24R- and 24S, 25-dihydroxycholesterol, compounds of formulas XII and XIII wherein $R_9$ $R_{10}$ are hydroxy, respectively, are solvolyzed with a strong acid in aqueous medium containing a miscible cosolvent. Suitable strong acids for this purpose include mineral acid such as hydrochloric acid, hydrobromic acid and sulfuric acid, and organic sulfonic acids such as benzenesulfonic acid, p-toluenesulfonic acid and the like. Sulfuric acid is preferred. As suitable miscible cosolvents, there may be mentioned ethereal solvents such as tetrahydrofuran and dioxane and ketones such as acetone and methyl ethyl ketone and the like. Ethereal solvents are preferred. Dioxane is most preferred.

While the retro-i-steroid rearrangement proceeds readily over a wide temperature range, it is preferable to perform the reaction within the temperature range of about 25° C to about the boiling point of the reaction medium. For most solvent systems, a reaction temperature of about 80° C is most preferred.

If one desires to prepare the 3-lower alkanoyloxy derivative, that is, a compound of formula XII or XIII wherein $R_9$ is lower alkanoyloxy and $R_{10}$ is hydroxy, one performs the retro-i-rearrangement in a solvent system containing the alkanoic acid corresponding to the alkanoyloxy group desired at the 3-position. For example, to prepare 24R 25-24S,25-dihydroxycholesteryl 3-acetate, one employes glacial acetic acid as the solvent medium. In this case, a strong acid is not required since the alkanoic acid solvent is sufficiently strong to serve as the acidic source. To promote the solvolysis reaction, sodium acetate is preferably added to the reaction medium, the reaction may be performed at an elevated temperature between about 40° C to about the boiling point of the reaction medium. A reaction temperature of about 60° C is most preferred.

If one desires to prepare the 3,24-di-(lower alkanoyloxy) derivative, that is, a compound of formula XII or XIII wherein $R_9$ and $R_{10}$ is lower alkanoyloxy, one carries out the reaction in a solvent medium comprising the lower alkanoic acid and lower alkanoic acid anhydride corresponding to the alkanoyloxy group desired at the 3-and 24-positions. For example, to prepare 24R,25-or 24S,25-dihydroxychlolesteryl 3,24-diacetate, one employs glacial acetic acid and acetic anhydride as the solvent medium and uses sodium acetate to promote the solvolysis. Elevated reaction temperatures falling within the range of about 40° C to about the boiling point of the solvent system may also be employed to promote the retro-i-rearrangement. A solvolysis reaction temperature of about 60° C is most preferred.

24R,25- and 24S,25-Dihydroxycholesterol and the alkanoyl derivatives thereof are useful intermediates for the preparation of the C-24-stereoisomers of the biologically important metabolite of vitamin $D_3$, 24R,25-dihydroxycholecalciferol and the unnatural 24S-stereoisomer by routes well-known in the art. This transformation is accomplished by introduction of the $\Delta^7$-double bond, generally by a halogenation-dehydrohalogenation process, followed by photolysis of the diene, thermal isomerization of the previtamin and hydrolysis of the alkanoyl groups, if necessary. See, for example, J. Redel, et al., supra, and H.-Y. Lam, et al., supra.

The following examples are illustrative of the invention and are not to be construed as limiting the invention in any manner.

All temperatures are given in °Centrigrade.

EXAMPLE 1

25;1 -Hydroxy-6β-methoxy-3α, 5-cyclo-5α-cholest-23-yne.

A mixture of 6β-methoxy-25-(2-tetrahydropyranyloxy)-3α, 5-cyclo-5α-cholest-23-yne (5.00 g, 0.0101 mole), p-toluenesulfonic acid monohydrate (0.1 g) and methanol (250 ml) was stirred at 0° for one hour. Potassium carbonate (1.0 g) was added and the mixture was stirred at 0°. After one-half hour the solvent was evaporated under reduced pressure. Water (200 was added to the residue and the mixture was extracted with ethyl acetate (2 × 100 ml). The combined organic layers were washed with water (100 ml) and saturated sodium chloride solution (100 ml) and dried over anhydrous magnesium sulfate. Evaporation of the solvent under vacuum after filtration of the drying agent, gave 4.10 g (99% ) of 256β-methoxy-3α, 5-cyclo-5α-cholest-23-yne. $[\alpha]_D^{25}$ + 49.7° (c 0.99, CHCl$_3$).

Anal. Calcd. for $C_{28}H_{44}O_2$ (MW 412.66): C, 81,50; H, 10.75; Found: C, 81.31; H, 10.79

EXAMPLE 2

25-Hydroxy-6β-methoxy-3α, 5-cyclo-5α-chlolest -23(E)-ene.

A mixture of 25-hydroxy-6β-methoxy-3α, 5-cyclo-5α-cholest-23-yne (1.20 g, 0.0029 mole), lithium aluminum hydride (1.65 g, 0.0063 mole) and tetrahydrofuran (50 ml) was heated under reflux for 48 hours with stirring. The reaction mixture was cooled to 0° , diluted with ether (100 ml), and water (3.3 ml) followed by 10% aqueous sodium hydroxide (2.6 ml) was added dropwise with stirring. The mixture was stirred at 0° for one hour. The solids were collected, triturated with methylene chloride and the mixture was filtered. The combined filtrates were evaporated and the residue dissolved in methylene chloride was filtered through a column of silica gel. Evaporation of the eluent followed by recrystallization of the residue from hexane gave 0.90 g (81%) of 25-hydroxy-6β-methoxy-3α, 5-cyclo-5α-cholest-23(E)-ene, m.p. 126°–127°.

$[\alpha]_D^{25}$ + 46.0 (c. 0.98, CHCl₃).

EXAMPLE 3

25-Hydroxy-6β-methoxy-3α,5-cyclo-5α-cholest-23(Z)ene.

A mixture of 25-hydroxy-6β-methoxy-3α,5-cyclo-5α-cholest-23-yne (0.312 g, 0.00076 mole), methanol (6 ml) and Lindlar catalyst (0.05 g), prepared from palladium supported on precipitated calcium carbonate, lead diacetate and quinoline according to the procedure described in "Organic Syntheses", Coll., Vol. V, John Wiley and Sons, New York, N.Y., 1973, pp. 880–883, was stirred under one atmosphere of hydrogen until the absorption of gas ceased. This required 24 hours. The reaction mixture was filtered through diatomaceous earth and the filtrate was evaporated to dryness to yield 0.310 g (99%) of 25-hydroxy-6β-methoxy-3α, 5-cyclo-5α-cholest-23(Z)-ene.

$[\alpha]_D^{25}$ + 37.4° (c 1.24, CHCl₃).

EXAMPLE 4

23R,24S-Epoxy-25-hydroxy-6β-methoxy-3α,5-cyclo-5α-cholestane.

A mixture of 25-hydroxy-6β-methoxy-3α,5-cyclo-5α-cholest-23(E)-ene (0.103 g, 0.00025 mole), vanadyl acetoacetate (0.001 g) and toluene (3 ml) was cooled to -78° and 90% tert-butyl hydroperoxide - 10% tert-butyl alcohol (0.060 g, 0.00060 mole) in toluene (3 ml) was added dropwise. After the addition was complete, the solution was stirred at -78° for 2 hours and then allowed to warm slowly to -20°. The solution was stirred at -20° for 6 hours. Methylene chloride (50 ml) was added to the reaction mixture and the solution was washed successively with saturated aqueous sodium bisulfite solution (25 ml) and water (25 ml). The organic phase was dried over anhydrous magnesium sulfate, filtered and the filtrate was concentrated under reduced pressure. Chromatography of the residue on silica gel gave 0.088 g (81%) of 23R,24S-epoxy-25-hydroxy-6β-methoxy-3α, 5- cyclo-5α-cholestane, m.p. 112°–113° by evaporation in the 2% acetone-methylene chloride fractions.

$[\alpha]_D^{25}$ + 52.9° (c 1.06, CHCl₃).

EXAMPLE 5

24S,25-Dihydroxy-6β-methoxy-3α, 5-cyclo-5α-cholestane.

To a solution of 1M borane in tetrahydrofuran (1 ml, 0.0010 mole) at 0° was added a solution of 25-hydroxy-6β-methoxy-3α,5-cyclo-5α-cholest-23 (E)-ene (0.104 g, 0.00025 mole) in tetrahydrofuran (1 ml) and the mixture was stirred at 0° for one hour and at 25° overnight. The reaction mixture was recooled to 0° and ice (0.10 g) was added to destroy the excess borane. 3N Aqueous sodium hydroxide solution (0.3 ml) and 30% aqueous hydrogen peroxide (0.3 ml) were successively added to the reaction mixture. The mixture was stirred for one hour, water (25 ml) was added and the solution was extracted with methylene chloride (3 × 25 ml). The combined organic extracts were washed with water (25 ml), dried over anhydrous magnesium sulfate, filtered and the filtrate was evaporated to dryness. The residue was dissolved in tetrahydrofuran (4 ml) and the solution was cooled to 0°. 0.1N Aqueous sulfuric acid (1 ml) was added dropwise and the mixture was stirred at 0° for 2 hours. Water (25 ml) was added and the solution was extracted with methylene chloride (3 × 25 ml). The combined organic extracts were washed with saturated aqueous sodium bicarbonate solution (2 × 25 ml), dried over anhydrous magnesium sulfate and filtered. Evaporation of the solvent under vacuum followed by recrystallization of the residue from benzene gave 0.060 g (55%) of 24S, 25-dihydroxy6α-methoxy- 3α,5-cyclo-5α-cholestane, m.p. 167°–168°.

$[\alpha]_D^{25}$ +38.2° (c 0.90, CHCl₃).

EXAMPLE 6

23R,24R-Epoxy-25-hydroxy-6β-methoxy-3α,5-cyclo-5α-cholestane.

A mixture of 25-hydroxy-6β-methoxy-3α,5-cyclo-5α-cholest-23(Z)-ene (0.103 g, 0.00025 mole), vanadyl acetoacetate (0.001 g) and toluene (3 ml) was cooled to −78° and 90% tert-butyl hydroperoxide - 10% tert-butyl alcohol (0.060 g, 0.00060 mole) in toluene (3 ml) was added dropwise. After the addition was complete, the solution was stirred at −78° for 2 hours and then allowed to warm slowly to −20°. The solution was stirred at −20° for 6 hours. Methylene chloride (50 ml) was added to the reaction mixture and the solution was washed successively with saturated aqueous sodium bisulfite solution (25 ml) and water (25 ml). The organic phase was dried over anhydrous magnesium sulfate, filtered and the filtrate was concentrated under reduced pressure. Chromatography of the residue on silica gel gave 0.083 g (77%) of 23R, 24R-epoxy-25-hydroxy-6β-methoxy-3α,5-cyclo-5α-cholestane

EXAMPLE 7

24R,25-Dihydroxy-6β-methoxy-3α,5-cyclo-5α-cholestane.

To a solution of 1M borane in tetrahydrofuran (1 ml, 0.0010 mole) at 0° was added a solution of 25-hydroxy-6β-methoxy-3α,5-cyclo-5α-cholest-23(Z)-ene (0.104 g, 0.00025 mole) in tetrahydrofuran (1 ml) and the mixture was stirred at 0° for one hour and at 25° overnight. The reaction mixture was recooled to 0° and ice (0.10 g) was added to destroy the excess borane. 3N Aqueous sodium hydroxide solution (0.3 ml) and 30% aqueous hydrogen peroxide (0.3 ml) were successively added to the reaction mixture. The mixture was stirred for one hour, water (25 ml) was added and the solution was extracted with methylene chloride (3 × 25 ml). The combined organic extracts were washed with water (25 ml), dried over anhydrous magnesium sulfate, filtered and the filtrate was evaporated to dryness. The residue was dissolved in tetrahydrofuran (4 ml) and the solution was cooled to 0°. 0.1N Aqueous sulfuric acid (1 ml) was added dropwise and the mixture was stirred at 0° for 2 hours. Water (25 ml) was added and the solution was extracted with methylene chloride (3 × 25 ml). The combined organic extracts were washed with saturated aqueous sodium bicarbonate solution (2 × 25 ml), dried over anhydrous magnesium sulfate and filtered. Evaporation of the solvent under vacuum followed by recrystallization of the residue from ethyl acetate gave 0.057 g (52%) of 24R,25-dihydroxy-6β-methoxy-3α,5-cyclo-5α-cholestane, m.p. 142°–143°.

$[\alpha]_D^{25}$ +62.1° (c 1.14, $CHCl_3$).

EXAMPLE 8

24S,25-Dihydroxy-6β-methoxy-3α,5-cyclo-5α-cholestane.

A mixture of 23R,24S,epoxy-25-hydroxy-6β-methoxy-3α,5-cyclo-5α-cholestane (0.046 g, 0.00011 mole), lithium aluminum hydride (0.038 g, 0.0010 mole) and tetrahydrofuran (2 ml) was stirred at 0° for one hour, at 25° for one hour and then cooled to 0° and diluted with ether (4 ml). Water (0.08 ml) and 10% aqueous sodium hydroxide solution (0.06 ml) were successively added and the mixture was stirred at 25° for one hour. The reaction mixture was filtered and the filtrate was evaporated. The residue was triturated with methylene chloride (3 × 10 ml), filtered and the combined filtrates were evaporated to dryness. Purification of the residual product by preparative thin layer chromatography on silica gel (1:1 benzene - ethyl acetate) afforded 0.022 g (47%) of 24S,25-dihydroxy-6β-methoxy-3α,5-cyclo-5α-cholestane, m.p. 167°-168°.

$[\alpha]_D^{25}$ +39.0° (c 0.88, $CHCl_3$).

EXAMPLE 9

24R,25-Dihydroxy-6β-methoxy-3α,5-cyclo-5α-cholestane.

A mixture of 23R,24R-epoxy-25-hydroxy-6β-methoxy-3α,5-cyclo-5α-cholestane (0.072 g, 0.00017 mole), lithium aluminum hydride (0.100 g, 0.0026 mole) and tetrahydrofuran (4 ml) was stirred at 0° for one hour and at 25° for one hour. The reaction mixture was diluted with ether (8 ml) and cooled to 0°. Water (0.20 ml) and 10% aqueous sodium hydroxide solution (0.16 ml) were successively added and the mixture was stirred at 25° for one hour. The reaction mixture was filtered, the filtrate was evaporated and the residue was triturated with methylene chloride (3 × 10 ml) and filtered. The combined filtrates were evaporated to dryness. Recrystallization from ethyl acetate afforded 0.062 g (86%) of 24R,25-dihydroxy-6β-methoxy-3α,5-cyclo-5α-cholestane, m.p. 142°-143°.

$[\alpha]_D^{25}$ +62.5° (c 0.96, $CHCl_3$).

EXAMPLE 10

24S,25-Dihydroxycholesterol.

A solution of 24S,25-dihydroxy-6β-methoxy-3α, 5-cyclo-5α-cholestane (0.108 g, 0.00025 mole), 0.1N aqueous sulfuric acid (1 ml) and dioxane (4 ml) was stirred at 80° for 4 hours. Water (50 ml) was added to the reaction mixture and the solution was extracted with methylene chloride (3 × 50 ml). The combined organic extracts were washed with saturated aqueous sodium bicarbonate solution (50 ml), dried over anhydrous magnesium sulfate and filtered. Recrystallization of the residue obtained by evaporation of the filtrate from methanol gave 0.085 g (81%) of 24S,25-dihydroxycholesterol, m.p. 196°-198°.

$[\alpha]_D^{25}$ −46.0° (c 0.99, $CH_3OH$).

EXAMPLE 11

24S,25-Dihydroxycholestesteryl 3-acetate.

A mixture of 24S,25-dihydroxy-6β-methoxy-3α,5-cyclo-5α-cholestane (0.200 g, 0.00046 mole) and 1M sodium acetate in acetic acid (3 ml) was heated for 32 hours at 60°. Methylene chloride (50 ml) was added to the reaction mixture and the solution was washed with water (25 ml) and then with saturated aqueous sodium bicarbonate solution (25 ml) and dried over anhydrous magnesium sulfate. Evaporation of the solvent, after removal of the drying agent by filtration, gave 0.210 g (99%) of 24S,25-dihydroxycholesteryl 3-acetate. Recrystallization from ethyl acetate gave a pure sample, m.p. 157°-158°.

$[\alpha]_D^{25}$ −58.3° (c 1.03, $CHCl_3$).

EXAMPLE 12

24S,25-Dihydroxycholesteryl 3,24-diacetate.

A mixture of 24S,25-dihydroxy-6β-methoxy-3α,5-cyclo-5α-cholestane (0.020 g, 0.000046 mole), acetic anhydride (0.024 g, 0.000235 mole) and 1M sodium acetate in acetic acid (1 ml) was stirred at 60° for 24 fours. Methylene chloride (25 ml) was added to the reaction mixture and the solution was washed with water (25 ml) and saturated aqueous sodium bicarbonate solution (25 ml) and dried over anhdyrous magnesium sulfate. Evaporation of the solvent after removal of the drying agent by filtration, and recrystallization of the residue from ethyl acetate gave 0.018 g (78%) of 24S,25-dihydroxycholesteryl 3,24-diacetate, m.p. 173°-174°.

$[\alpha]_D^{25}$ −40.9° (c 0.99, $CHCl_3$)

EXAMPLE 13

24R,25-Dihydroxycholesterol.

A solution of 24R,25-dihydroxy-6β-methoxy-3α,5-cyclo-5α-cholestane (0.194 g, 0.00045 mole), 0.1N aqueous sulfuric acid (2 ml) and dioxane (6 ml) was stirred at 80° for 4 hours. Water (50 ml) was added to the reaction mixture and the solution was extracted with methylene chloride (3 × 50 ml). The combined organic extracts were washed with saturated aqueous sodium bicarbonate solution (50 ml), dried over anhydrous magnesium sulfate and filtered. Recrystallization of the residue obtained by evaporation of the solvent gave 0.150 g (79%) of 24R, 25 -dihydroxycholesterol, m.p. 200°-202°. $[\alpha]D/25$ -11.6° (c 0.93, $CH_3OH$).

EXAMPLE 14

24R, 25-Dihydroxycholesteryl 3-acetate.

A solution of 24S, 25-dihydroxy-6β-methoxy-3α, 5-cyclo-5α-cholestane (0.200 g, 0.00046 mole) and 1M sodium acetate in acetic acid (3 ml) was heated at 60° for 24 hours. Methylene chloride (25 ml) was added to the reaction mixture and the solution was washed with water (25 ml) and then with saturated aqueous sodium bicarbonate solution (25 ml) and dried over anhydrous magnesium sulfate. The drying agent was collected on a filter and the filtrate was evaporated. Recrystallization of the residue from ethyl acetate afforded 0.187 g (88%) of 24R, 25-dihydroxycholesteryl 3-acetate, m.p. 164°-165°. $[\alpha]D/25$ −31.2° (c 0.95, $CHCl_3$).

EXAMPLE 15

24R, 25-Dihydroxycholesteryl 3,24-diacetate.

A mixture of 24R, 25-dihydroxy-6β-methoxy-3α, 5-cyclo-5α-chloestane (0.030 g, 0.00007 mole), acetic anhydride (0.020 g, 0.00020 mole) and 1M sodium acetate ina cetic acid (1 ml) was stirred at 60° for 24 hours. Water (25 ml) was added to the reaction mixture and the solution was extracted with methylene chloride (3 × 25 ml). The combined organic layers were washed with saturated aqueous sodium bicarbonate solution (2 × 25 ml), dried over anhydrous magnesium sulfate and filtered. Evaporation of the filtrate followed by recrystallization of the residue afforded 0.030 g (85%) of 24R, 25-dihydroxychloesteryl 3,24-diacetate, m.p. 122°–123°. [α]D/25 −36.8°(c 1.10, CHCl₃).

We claim:

1. A process for the preparation of a compound of the formula

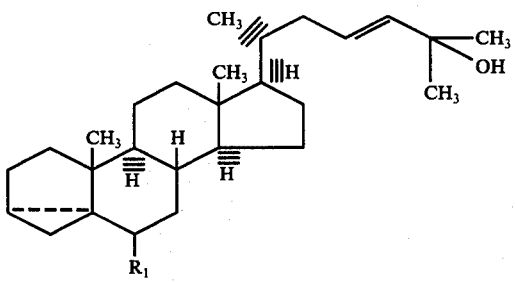

wherein R₁ is hydroxy, lower alkoxy, phenyl lower alkoxy, lower alkanoyloxy or benzoyloxy and the configuration of the 23, 24-double bond it trans, i.e., where the 23, 24-double bond has the E-configuration, which comprises contacting a compound of the formula

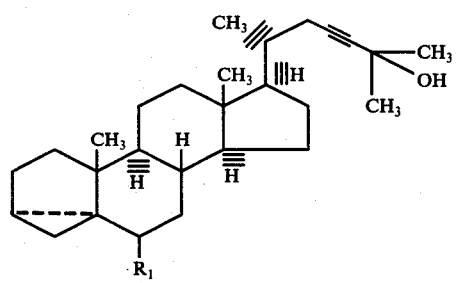

wherein R₁ is as above, with a complex metal hydride reducing agent in an etheral organic solvent.

2. The process of claim 1 wherein R₁ is lower alkoxy.
3. The process of claim 2 wherein R₁ is methoxy.
4. The process of claim 1 wherein the complex metal hydride reducing agent is an alkali metal aluminum hydride.
5. The processs of claim 4 wherein the alkali metal aluminum hydride is lithium aluminum hydride.
6. The process of claim 1 wherein the etheral solvent is tetrahydrofuran.
7. A process for the preparation of a compound of the formula

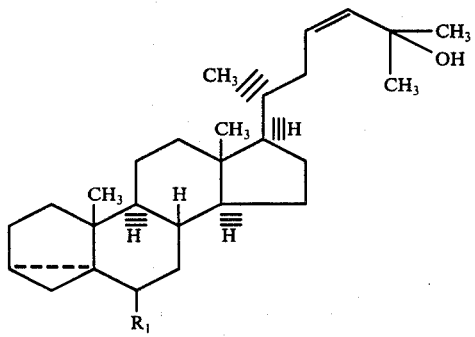

wherein R₁ is hydroxy, lower alkoxy, phenyl lower alkoxy, lower alkanoyloxy or benzoyloxy and the configuration of the 23.24-double bond is cis i.e., wherein the 23,24-double bond has the Z-configuration, which comprises treating the compound of the formula

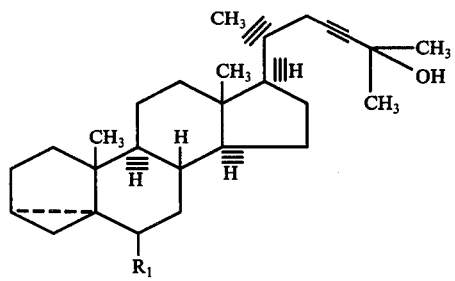

wherein R₁ is as above with hydrogen in the presence of Lindlar catalyst and an inert solvent.

8. The process of claim 7 wherein R₁ is lower alkoxy.
9. The process of claim 8 wherein R₁ is methoxy.
10. A process for the preparation of the compound of the formula

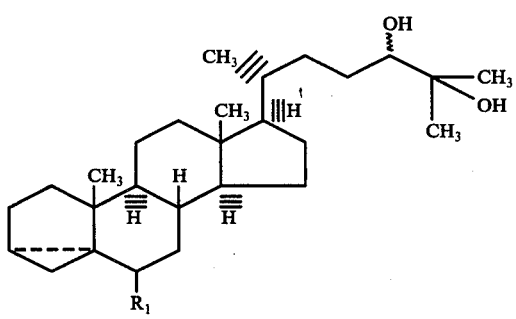

wherein R₁ is hydroxy, lower alkoxy, phenyl lower alkoxy, lower alkanoyloxy or benxoyloxy and the absolute configuration of the C-24 hydroxyl group is R or S, which comprises a. contacting a compound of the formula

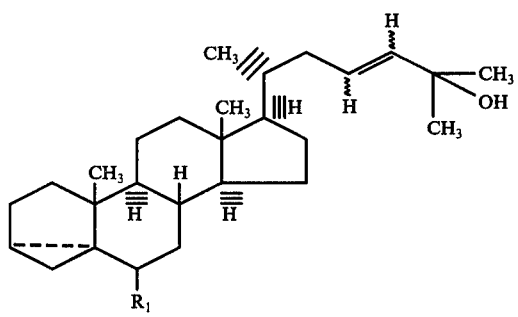

wherein R₁ is as above and the configuration of the C-23, C-24 double bond is cis, that is, denoted by the symbol Z, or trans, that is, denoted by the symbol E, with a lower alkyl or aryl lower alkyl hydroperoxide in the presence of a compound of the formula

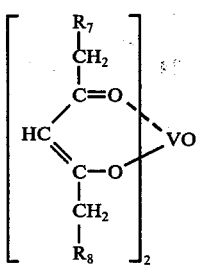

wherein $R_7$ and $R_8$ are hydrogen or lower alkyl in the inert solvent at a reduced temperature to afford a compound of the formula

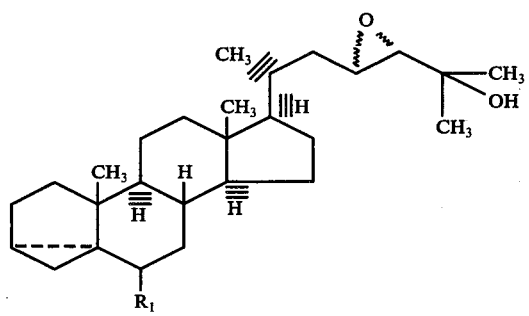

wherein $R_1$ is as above and the absolute configuration of the C-23, C-24 epoxy group is 23R, 24S or 23R, 24R, and b. treating said product with a complex metal hydride reducing agent in an inert solvent at reduced temperature.

11. The process of claim 10 wherein $R_1$ is lower alkoxy.

12. The process of claim 11 wherein $R_1$ is methoxy.

13. The process of claim 10 wherein the lower alkyl hydroperoxide is a lower tertiary alkyl hydroperoxide.

14. The process of claim 13 wherein the lower tertiary alkyl hydroperoxide is tertiary-butyl hydroperoxide.

15. The process of claim 13 wherein the aryl lower alkyl hydroperoxide is cumyl hydroperoxide.

16. The process of claim 10 wherein $R_7$ and $R_8$ are hydrogen.

17. The process of claim 10 wherein the inert organic solvent in step (a) is an aromatic solvent.

18. The process of claim 17 wherein the aromatic solvent is toluene.

19. The process of claim 10 wherein the reduced temperature of step (a) is about $-78°$ C to about $-20°$ C.

20. The process of claim 10 wherein the complex metal hydride reducing agent is an alkali metal aluminum hydride.

21. The process of claim 20 wherein the alkali metal aluminum hydride is lithium aluminum hydride.

22. The process of claim 10 wherein the inert organic solvent of step (b) is an ethereal solvent.

23. The process of claim 22 wherein the ethereal solvent is tetrahydrofuran.

24. The process of claim 10 wherein the reduced temperature of step (b) is about $0°$ C.

25. A process for the preparation of a compound of the formula

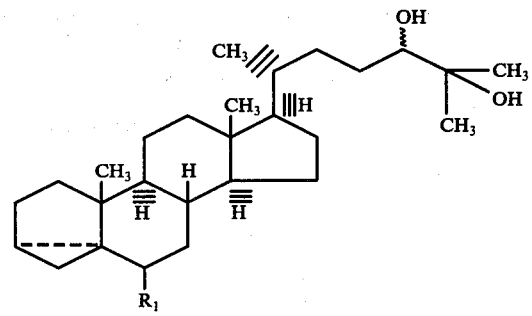

wherein $R_1$ is hydroxy, lower alkoxy, phenyl lower alkoxy, lower alkanoyloxy or benzoyloxy and the absolute configuration of the C-24 hydroxyl group is R or S, which comprises a. contacting a compound of the formula

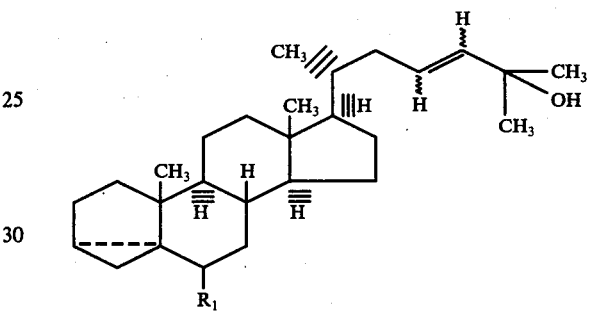

wherein $R_1$ is as above and the configuration of the C-23, C-24 double bond is cis, that is, denoted by the symbol Z, or trans, that is, denoted by the symbol E, with a borane of the formula

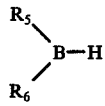

wherein $R_5$ and $R_6$ each taken independently are hydrogen, alkyl or cycloalkyl and $R_5$ and $R_6$ taken together are lower alkylene in an inert organic solvent at a reduced temperature to afford a compound of the formula

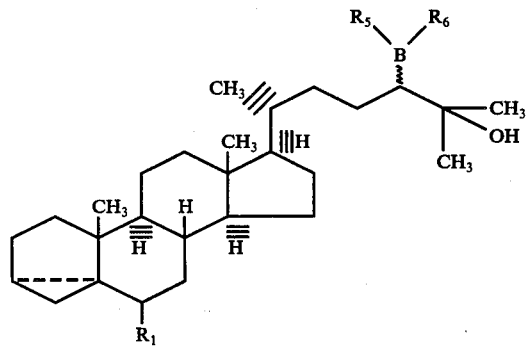

wherein $R_1$, $R_5$ and $R_6$ are as above; and b. contacting said product with an oxidizing agent in an inert organic solvent.

26. The process of claim 25 wherein $R_5$ and $R_6$ each taken independently are hydrogen, alkyl or cycloalkyl.

27. The process of claim 26 wherein $R_5$ and $R_6$ each taken indenpendently are hydrogen.

28. The process of claim 25 wherein the inert organic solvent of step (a) is an ethereal solvent.

29. The process of claim 28 wherein the ethereal solvent is tetrahydrofuran.

30. The process of claim 25 wherein the reduced temperature is about $-25°$ C to about $+40°$ C.

31. The process of claim 25 wherein the reduced temperature is about $0°$ C to about $+25°$ C.

32. The process of claim 25 wherein $R_1$ is lower alkoxy.

33. The process of claim 32 wherein $R_1$ is methoxy.

34. The process of claim 25 wherein the oxidizing agent is aqueous alkaline 30% hydrogen peroxide at a reduced temperature of about $0°$ C. to about $30°$ C.

35. The process of claim 34 wherein the alkali is alkali metal hydroxide.

36. The process of claim 35 wherein the alkali metal hydroxide is sodium hydroxide.

37. A process for the preparation of a compound of the formula

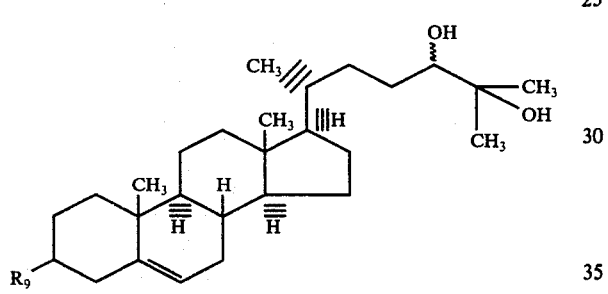

wherein $R_9$ is hydroxy or lower alkanoyloxy and the absolute configuration of the C-24 hydroxyl group is R or S, which comprises treating a compound of the formula

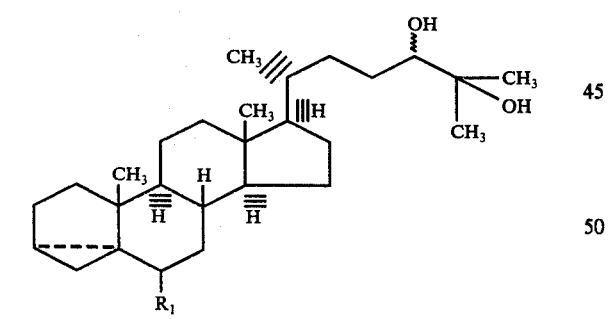

wherein $R_1$ is hydroxy, lower alkoxy, phenyl lower alkoxy, lower alkanoyloxy or benzoyloxy, and the absolute configuration of the C-24 hydroxyl group is R or S,
with an acid in a solvent medium comprising $R_9H$, wherein $R_9$ is as above, at a temperature between about 25° C and about 100° C.

38. The process of claim 37 wherein $R_1$ is lower alkoxy.

39. The process of claim 38 wherein $R_1$ is methoxy.

40. The process of claim 37 wherein the acid is sulfuric acid or an organic sulfonic acid.

41. The process of claim 40 wherein the acid is sulfuric acid.

42. The process of claim 37 wherein the solvent medium comprises water.

43. The process of claim 37 wherein the solvent medium comprises acetic acid.

44. A process for the preparation of a compound of the formula

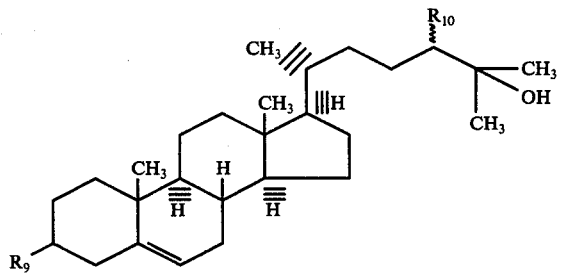

wherein $R_9$ and $R_{10}$ are lower alkanoyloxy, and the absolute configuration of the C-24 alkanoyloxy group is R or S,
which comprises contacting a compound of the formula

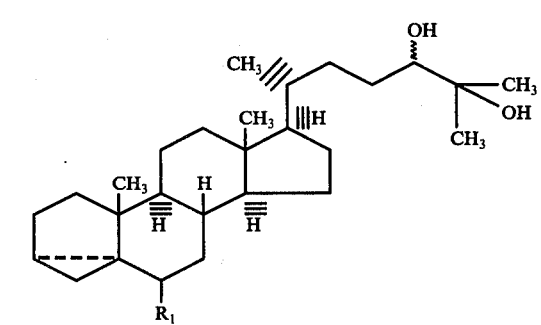

wherein $R_1$ is hydroxy, lower alkoxy, phenyl lower alkoxy, lower alkanoyloxy or benzoyloxy and the absolute configuration of the C-24 hydroxyl group is R or S,
with an acid comprising $R_9$ H wherein $R_9$ is lower alkanoyloxy in a solvent medium comprising $R_9H$ and $(R_9)_2O$, wherein $R_9$ is lower alkanoyloxy, at a temperature between about 25° C and about 100° C.

45. The process of claim 44 wherein $R_1$ is lower alkoxy.

46. The process of claim 45 wherein $R_1$ is lower methoxy.

47. The process of claim 44 wherein the acid comprises acetic acid.

48. The process of claim 44 wherein the solvent medium comprises acetic acid and acetic anhydride.

49. A compound of the formula

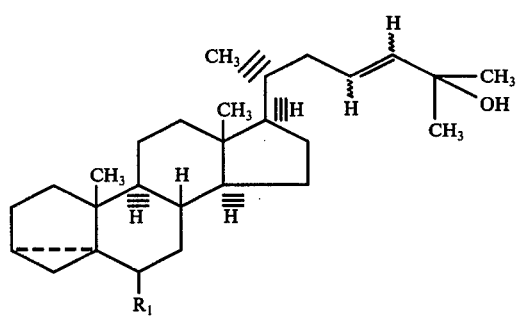

wherein R₁ is hydroxy, lower alkoxy, phenyl lower alkoxy, lower alkanoyloxy or benzoyloxy and the configuration of the C-23, C-24 double bond is cis, that is, denoted by the symbol Z, or trans, that is, denoted by the symbol E.

50. The compound of claim 49 wherein R₁ is lower alkoxy.

51. The compound of claim 50 wherein R₁ is methoxy.

52. The compound of claim 49 wherein the configuration of the 23,24-double bond is cis, that is, denoted by Z.

53. The compound of claim 49 wherein the configuration of the 23,24-double bond is trans, that is, denoted by E.

54. A compound of the formula

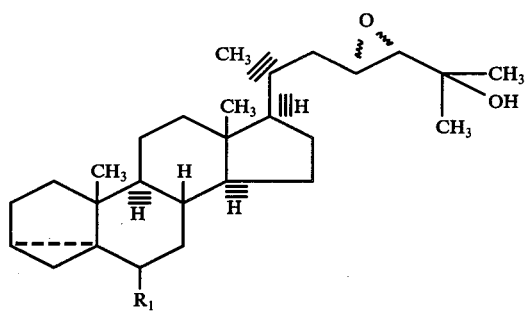

wherein R₁ is hydroxy, lower alkoxy, phenyl lower alkoxy, lower alkanoyloxy or benzoyloxy.

55. The compound of claim 54 wherein R₁ is lower alkoxy and the absolute configuration of the epoxy group is 23R,24S or 23R,24R.

56. The compound of claim 55 wherein R₁ is methoxy and the absolute configuration of the epoxy group is 23R,24S.

57. The compound of claim 55 wherein R₁ is methoxy and the absolute configuration of the epoxy group is 23R,24R.

58. A compound of the formula

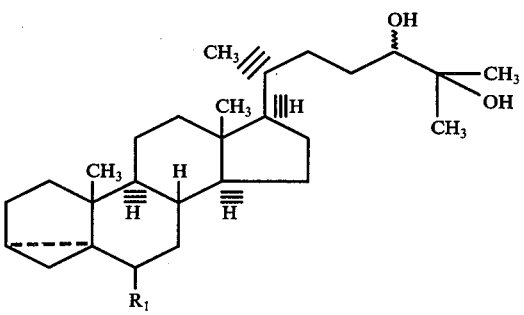

wherein R₁ is hydroxy, lower alkoxy, phenyl lower alkoxy, lower alkanoyloxy or benzoyloxy.

59. The compound of claim 58 wherein R₁ is lower alkoxy and the absolute configuration of the C-24 hydroxyl group is R or S.

60. The compound of claim 59 wherein R₁ is methoxy and the absolute configuration of the C-24 hydroxyl group is R.

61. The compound of claim 59 wherein R₁ is methoxy and the absolute configuration of the C-24 hydroxyl group is S.

62. The compound of claim 49 which is 25-hydroxy-6β-methoxy-3α,5-cyclo-5α-cholest-23(E)-ene.

63. The compound of claim 49 which is 25-hydroxy-6β-methoxy-3α,5-cyclo-5α-cholest-23(Z)-ene.

* * * * *

UNITED STATES PATENT AND TRADEMARK OFFICE
CERTIFICATE OF CORRECTION

PATENT NO. : 4,038,272
DATED : July 26, 1977
INVENTOR(S) : John Joseph Partridge, Jr. and Milan Radoje Uskokovic It is certified that error appears in the above-identified patent and that said Letters Patent are hereby corrected as shown below:

Column 17, claim 1, line 23, "it trans" should be is trans.

Column 17, claim 6, line 50, "etheral" should be ethereal.

Column 18, claim 7, line 3, "23.24-double bond" should be 23,24-double bond.

Column 18, claim 10, line 43, "benxoyloxy" should be benzoyloxy.

Column 19, claim 10, line 15, "in the inert solvent" should be in an inert solvent.

Column 21, claim 37, line 61, "25° C and about" should be 25° C to about.

Column 22, claim 44, line 45, "25° C and about" should be 25° C to about.

Column 22, claim 46, line 49, "lower methoxy" should be methoxy.

Signed and Sealed this

Twenty-seventh Day of November 1979

[SEAL]

Attest:

RUTH C. MASON
Attesting Officer

LUTRELLE F. PARKER
Acting Commissioner of Patents and Trademarks